US007709440B2

(12) United States Patent
Shaari

(10) Patent No.: US 7,709,440 B2
(45) Date of Patent: May 4, 2010

(54) TREATING NEOPLASMS WITH NEUROTOXIN

(75) Inventor: Christopher Shaari, Demarest, NJ (US)

(73) Assignee: Toxcure, Inc., Hackensack, NJ (US)

(*) Notice: Subject to any disclaimer, the term of this patent is extended or adjusted under 35 U.S.C. 154(b) by 0 days.

(21) Appl. No.: 11/577,838

(22) PCT Filed: Sep. 23, 2005

(86) PCT No.: PCT/US2005/033982

§ 371 (c)(1),
(2), (4) Date: Apr. 24, 2007

(87) PCT Pub. No.: WO2006/034404

PCT Pub. Date: Mar. 30, 2006

(65) Prior Publication Data

US 2009/0028972 A1   Jan. 29, 2009

Related U.S. Application Data

(60) Provisional application No. 60/612,443, filed on Sep. 23, 2004.

(51) Int. Cl.
   *A01N 37/18* (2006.01)
(52) U.S. Cl. .......................... 514/2; 530/350
(58) Field of Classification Search ................ None
   See application file for complete search history.

(56) References Cited

U.S. PATENT DOCUMENTS

| 5,766,605 A | 6/1998 | Sanders et al. |
| 6,139,845 A | 10/2000 | Donovan |
| 6,565,870 B1 | 5/2003 | Donovan |
| 2001/0021695 A1 | 9/2001 | Aoki |
| 2002/0094339 A1 | 7/2002 | Donovan et al. |
| 2005/0031648 A1* | 2/2005 | Brin et al. ............... 424/239.1 |
| 2006/0286127 A1 | 12/2006 | Van Schaack |

FOREIGN PATENT DOCUMENTS

| EP | 1 599 218 | 11/2005 |
| EP | 1 604 678 | 12/2005 |
| EP | 1 804 827 | 7/2007 |
| EP | 1 890 714 | 2/2008 |
| EP | 1 990 059 | 11/2008 |
| WO | WO 0178760 | 10/2001 |
| WO | WO 0182961 | 11/2001 |
| WO | WO 0207759 | 1/2002 |
| WO | WO 0209743 | 2/2002 |
| WO | WO 2004071525 | 8/2004 |
| WO | WO 2004/076634 | 9/2004 |
| WO | WO 2004078202 | 9/2004 |
| WO | WO 2005/030248 | 4/2005 |
| WO | WO 2006025976 | 3/2006 |
| WO | WO 2006/094539 | 9/2006 |
| WO | WO 2006138059 | 12/2006 |

OTHER PUBLICATIONS

Lang et al, Methods in Ezymology, 2005, 1995, 256:320-327.*
Valitutti et al, J Exp Med, 1995, 181:577-584.*
Woodside et al, J Exp Med, 1998, 188:1211-1221.*
Gura, Science, 1997, 278:1041-1042.*
Shantz, E. J., et al., "Properties and Use of Botulinum Toxin and Other Microbial Neurotoxins in Medicine," Microbiol Rev. 56: pp. 80-99 (1992).
Targarona, E. M., et al., World J Surg 22, pp. 57-58 (1998).
Hiroto, M. et al., Journal of Pancreas 6(2): pp. 143-151 (2005).
Whiteside, T. L., Allergy Clin Immunol 111: pp. S677-S686 (2003).
Qiu, Y. H., Peng, Y. P., et al. "Effect of acetylcholine on in vitro IL-2 production and NK cell cytotoxicity of rats," Lymphology 37(1): pp. 31-38 (2004).
Black, et al. Cell Biol. 103(2): pp. 535-544 (1986).
Hesse, et al. Neurosci Lett. 201(1): pp. 37-40 (1995).
Hesse, et al. Clin Rehabli 12(5): p. 3810388 (1998).
Noguera, et al. "Botulinum Toxin in the Treatment of Spasticity in HIV-infected Children Affected with Progressive Encephalopathy," AIDS 18(2): (2004).

(Continued)

*Primary Examiner*—Misook Yu
*Assistant Examiner*—Mark Halvorson
(74) *Attorney, Agent, or Firm*—Frommer Lawernce & Haug LLP; Edgar H. Haug; Heather J. DiPietrantonio

(57) ABSTRACT

The present invention provides a method of treating a cancer using a neurotoxin, preferably Botulinum toxin ("BTX"). The application of a neurotoxin around a cancer acts to decrease the contractile forces of the muscles surrounding a neoplasm which normally squeeze cancer cells through efferent channels leaving the cancer vicinity to distant sites. Also, the application of the toxin at sites distant from the cancer enhances cellular and humoral immunologic functions which further contributes to cancer cell death and spread. Following administration of botulinum toxin around and distant to a cancer, it is noticed that local, regional, and distant spread is reduced or eliminated. Immunomodulation with botulinum toxin is also valuable in treating other disease that may or may not be associated with cancers, such as viral-induced growths, viral conditions, fungal disease, chronic wounds, graft versus host disease, autoimmune disease, and HIV.

9 Claims, No Drawings

OTHER PUBLICATIONS

Childers M. K., et al. "Comparison of Two Injection Technique Using Botulinum Toxin in Spastic Hemiplegia," American Journal of Physical Medicine & Rehabilitation/Association of Academic Physiatrists. 75(6): pp. 462-469 (1996).

Tang-Liu, et al. "Intramuscular Injection of $^{125}$I-botulinum Neurotoxin-Complex Versus $^{125}$I-botulinum-free Neurotoxin: Time Course of Tissue Distribution," Toxicon 42: pp. 461-469 (2003).

Ansiaux, R. et al., "Botulinum Toxin Potentiates Cancer Radiotherapy and Chemotherapy," Clin Cancer Res 12(4): pp. 1276-1283 (2006).

Supplemental European Search Report mailed on Jan. 28, 2008 for European Application No. EP 5 814 023.

International Search Report mailed on Jun. 12, 2006 for International Application No. PCT/US05/33982.

Shaari and Sanders, Quantifying How Location and Dose of Botulinum Toxin Injections Affect Muscle Paralysis, Muscle and Nerve, 1993, vol. 16, pp. 964-969.

Shaari, et al., Botulinum Toxin Decreases Salivation from Canine Submandibular Glands, Otolaryngology-Head and Neck Surgery, 1998, vol. 118, pp. 452-457.

Shaari, et al. Rhinorrhea is decreased in Dogs After the Nasal Application of Botulinum Toxin, Otolaryngology-Head and Neck Surgery, 1995, vol. 112, pp. 566-571.

Shaari, et al., Quantifying the Spread of Botulinum Toxin Through Muscle Fascia, Laryngoscope, 1991, vol. 101, pp. 960-964.

Shaari, et al., Study of Botulinum Toxin Injection Parameters, Report of Defense of Dissertation M.D. with Distinction in Research Albany medical College Archives, Mar. 11, 1991.

Shaari and Sanders, The Assessment of Biologic Activity of Botulinum Toxin, In: Jankovic J. Hallett M, eds. Therapy with Botulinum Toxin, New York, New York, Marcel Dekker, Inc., 1994, pp. 159-170.

European Patent Office Communication mailed Sep. 2, 2009 in European Application No. 05 814 023.

* cited by examiner

TREATING NEOPLASMS WITH NEUROTOXIN

This application claims priority from provisional U.S. application No. 60/612,443, filed Sep. 23, 2004.

BACKGROUND

The present invention relates to methods for treating various benign or malignant neoplasms, chronic infections, autoimmune diseases, and immunodeficiencies. In particular, the present invention relates to methods of treating the growth and metastasis of various malignancies with a botulinum toxin.

Neoplasms

The initial growth of neoplasms is dependent upon adequate supply of growth factors and the removal of toxic molecules. The expansion of tumor mass beyond 2 mm in diameter depends on the development of angiogenesis to produce adequate blood supply. The induction of angiogenesis is mediated by multiple molecules that are released by both tumor cells and host cells, including endothelial cells, epithelial cells, mesothelial cells, and leukocytes. Angiogenesis consists of sequential processes emanating from microvascular endothelial cells. As it expands, the tumor (primary or secondary) can also cause certain symptoms, such as discomfort (e.g., the feeling of a lump), pain and bleeding.

After angiogenesis begins, tumor cell invasion of the tissue surrounding the primary tumor and penetration of blood and lymph vessels is central to the whole phenomenon of metastasis.

Once tumor cells detach from the primary tumor, they must invade the host stroma to penetrate lymphatics and blood vessels. To do so, tumor cells must penetrate basement membranes surrounding blood vessels. Basement membranes and connective tissue extracellular matrix (ECM) consist of four major groups of molecules: collagens, elastins, glycoproteins, and proteoglycans. The degradation of the ECM and basement membrane components by tumor cells is an essential prerequisite for invasion and metastasis.

In sum, cancer metastasis consists of multiple complex, interacting, and interdependent steps, each of which is rate-limiting, since a failure to complete any of the steps prevents the tumor cell from producing a metastasis. The tumor cells that eventually give rise to metastases must survive a series of potentially lethal interactions with host homeostatic mechanisms. The balance of these interactions can vary among different patients with different neoplasms or even among different patients with the same type of neoplasm.

The essential steps in the formation of a metastasis are similar in all tumors and consist of the following:
1. Alter neoplastic transformation, progressive proliferation of neoplastic cells is initially supported with nutrients supplied from the organ microenvironment by diffusion.
2. Neovascularization or angiogenesis must take place for a tumor mass to exceed 1 or 2 mm in diameter. The synthesis and secretion of different angiogenic molecules and suppression of inhibitory molecules are responsible for the establishment of a capillary network from the surrounding host tissue.
3. Some tumor cells can down regulate expression of cohesive molecules and have increased motility and, thus, can detach from the primary lesion. Invasion of the host stroma by some tumor cells occurs by several parallel mechanisms. Capillaries and thin-walled venules, like lymphatic channels, offer very little resistance to penetration by tumor cells and provide the most common pathways for tumor cell entry into the circulation.
4. Detachment and embolization of single tumor cells or cell aggregates occur next, the vast majority of circulating tumor cells being rapidly destroyed.
5. Once the tumor cells have survived the circulation, they must . . . .
6. Arrest in the capillary beds of distant organs by adhering either to capillary endothelial cells or to exposed subendothelial basement membranes.
7. Tumor cells (especially those in aggregates) can proliferate within the lumen of the blood vessel, but the majority extravasate into the organ parenchyma by mechanisms similar to those operative during invasion.
8. Tumor cells bearing appropriate cell surface receptors can respond to paracrine growth factors and hence proliferate in the organ parenchyma.
9. The metastatic cells must evade destruction by host defenses that include specific and nonspecific immune responses.
10. To exceed a mass of 1 to 2 mm in diameter, metastasis must develop a vascular network.

Botulinum Toxin

The anaerobic, gram positive bacterium Clostridium botulinum produces a potent polypeptide neurotoxin, botulinum toxin. To date seven immunologically distinct botulinum neurotoxins have been characterized: serotypes A, B, $C_1$, D, E, F, and G. Of these Botulinum toxin type A is recognized as one of the most lethal naturally occurring agents known to man.

It is postulated that the botulinum toxins bind with high affinity to cholinergic motor neurons, are transferred into the neuron and effectuate blockade of the presynaptic release of acetylcholine. All of the botulinum toxin serotypes are purported to inhibit release acetylcholine at the neuromuscular junction, they do so by affecting different neurosecretory proteins and/or cleaving these proteins at different sites. For example, Botulinum toxin A is a zinc endopeptidase which can specifically hydrolyze a peptide linkage of the intracellular, vesicle associated protein SNAP-25. Botulinum type E also cleaves the 25 kiloDalton (kD) synaptosomal associated protein (SNAP-25), however, type E binds to a different amino acid sequence within SNAP-25. It is believed that differences in the site of inhibition is responsible for the relative potency and/or duration of action of the various botulinum toxin serotypes.

Currently, Botulinum toxins have been used in clinical settings for the treatment of neuromuscular disorders characterized by hyperactive skeletal muscles. Botulinum toxin type A was approved by the U.S. Food and Drug Administration in 1989 for the treatment of essential blepharospasm, strabismus and hemifacial spasm in patients over the age of twelve. In 2000, the FDA approved commercial preparations of type A and type B botulinum toxin serotypes for the treatment of cervical dystonia, and in 2002 the FDA approved a type A botulinum toxin for the cosmetic treatment of certain hyperkinetic (glabellar) facial wrinkles. In 2004, the FDA approved botulinum for the treatment of hyperhidrosis. Non-FDA approved uses hemifacial spasm, spasmodic torticollis, oromandibular dystonia, spasmodic dysphonia and other dystonias, tremor, myofascial pain, temporomandibular joint dysfunction, migraine, spasticity.

Clinical effects of peripheral intramuscular botulinum toxin type A are usually seen within 24-48 hours of injection and sometimes within a few hours. When used to induce muscle paralysis, symptomatic relief from a single intramuscular injection of botulinum toxin type A can last approximately three months, however, under certain circumstances effects have been known to last for several years.

Despite the apparent difference in serotype binding, it is thought that the mechanism of botulinum activity is similar and involves at least three steps. First, the toxin binds to the presynaptic membrane of a target cell. Second, the toxin enters the plasma membrane of the effected cell wherein an endosome is formed. The toxin is then translocated through the endosomal membrane into the cytosol. Third, the botulinum toxin appears to reduce a SNAP disulfide bond resulting in disruption in zinc (Zn++) endopeptidase activity, which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and C.sub.1 are apparently produced as only a 500 kD complex. Botulinum toxin type D is produced as both 300 kD and 500 kD complexes. Finally, botulinum toxin types E and F are produced as only approximately 300 k) complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The toxin complexes can be dissociated into toxin protein and hemagglutinin proteins by treating the complex with red blood cells at pH 7.3. The toxin protein has a marked instability upon removal of the hemagglutinin protein.

All the botulinum toxin serotypes are made by Clostridium botulinum bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes C.sub.1, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for a lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

High quality crystalline botulinum toxin type A can be produced from the Hall A strain of Clostridium botulinum with characteristics of 3.times.10.sup.7 U/mg, an A.sub.260/A.sub.278 of less than 0.60 and a distinct pattern of banding on gel electrophoresis. The known Shantz process can be used to obtain crystalline botulinum toxin type A, as set forth in Shantz, E. J., et al, Properties and use of Botulinum toxin and Other Microbial Neurotoxins in Medicine, Microbiol Rev. 56: 80-99 (1992). Generally, the botulinum toxin type A complex can be isolated and purified from an anaerobic fermentation by cultivating Clostridium botulinum type A in a suitable medium. Raw toxin can be harvested by precipitation with sulfuric acid and concentrated by ultramicrofiltration. Purification can be carried out by dissolving the acid precipitate in calcium chloride. The toxin can then be precipitated with cold ethanol. The precipitate can be dissolved in sodium phosphate buffer and centrifuged. Upon drying there can then be obtained approximately 900 kD crystalline botulinum toxin type A complex with a specific potency of 3.times.10.sup.7 LD.sub.50 U/mg or greater. This known process can also be used, upon separation out of the non-toxin proteins, to obtain pure botulinum toxins, such as for example: purified botulinum toxin type A with an approximately 150 kD molecular weight with a specific potency of 1-2.times.10.sup.8 LD.sub.50 U/mg or greater; purified botulinum toxin type B with an approximately 156 kD molecular weight with a specific potency of 1-2.times.10.sup.8 LD.sub.50 U/mg or greater, and; purified botulinum toxin type F with an approximately 155 kD) molecular weight with a specific potency of 1-2.times.10.sup.7 LD.sub.50 U/mg or greater.

Already prepared and purified botulinum toxins and toxin complexes suitable for preparing pharmaceutical formulations can be obtained from List Biological Laboratories, Inc., Campbell, Calif.; the Centre for Applied Microbiology and Research, Porton Down, U.K.; Wako (Osaka, Japan), as well as from Sigma Chemicals of St Louis, Mo.

The pattern of toxin spread within a muscle has been demonstrated to be related to concentration, volume and location of injection site (22).

Prior Art Using a Neurotoxin to Treat Cancer

Several patents and applications have taught treating cancers with a neurotoxin and specifically a botulinum toxin. Uniformly, the methods have taught to directly deliver botulinum toxin to the cancerous cells or their vicinity with the goal of directly affecting the cancerous cells or their innervation. The goal has been to deliver the toxin into the cancerous cell to exert an effect, or to locally denervate a cancerous cell.

By getting the toxin into a cell, botulinum toxin may inhibit the process of exocytosis from the cancer cell, which is the release of a cell's intracellular contents or vesicles into the extracellular space. These patents and applications teach, in part, that inhibiting exocytosis of a cancer cell will reduce the activity of a cells division and reduce the ability of the cancer cell to move. By locally denervating a cancer cell, it may become less active. The following review of prior art will address these issues.

Patent application US2005/0031648 A1, *Methods for Treating Diverse Cancers*, discloses the treatment of hyperplastic, precancerous or cancerous tissues with a botulinum neurotoxin by locally administering the botulinum toxin to the hyperplastic, precancerous or cancerous tissue or to its vicinity. Only diseased tissue is "treated." Local administration is defined as direct injection of the neurotoxin into or to the local area of the target tissue (para 178). "Treatment" is defined as specifically causing the reduction in the size and or activity of a hyperplastic, hypertonic or neoplastic tissue, by targeting the cancer cells directly or the "vicinity of the target tissue" (para 159). This patent application further states that a "therapeutically effective amount" will not cause significant negative or adverse side effects to the treated tissue (para 177). The patent application acknowledges that in order to achieve the desired effect in a non-neuronal cell (such as a breast cancer) the injected dose may need to be higher (0187) since non-nerve cells do not contain cell surface receptors for a botulinum toxin. In fact, such cells must be permeabilized to allow entry in vitro of the botulinum toxin into the cells cytosol (para 191). In addition, this patent application states that a botulinum toxin can block the release of any vesicle mediated endocytosis as long as the light chain of the botulinum toxin is translocated into the intracellular medium (para 191).

Patent application WO 2005/030248 attempts to overcome the significant shortfall of botulinum toxin when directly treating cancer cells, namely that the toxin does not have a high affinity for non-neuronal cells and therefore much higher doses are needed to enter such a cell. Once the toxin is into a cell, the toxin will interfere with the intracellular machinery. This application describes a method of increasing the entry of botulinum toxin c3 into cancer cells by linking the c3 to a cell-permeable fusion protein. The goal of the treatment is to stop the cancer cell from contracting and spreading. The described compound specifically targets a cancer cell. This patent application teaches that the compound can be injected around a cancer at the 'resection margin' following surgery as well, but the goal is to treat cancerous cells that may reside at that margin. The method of injection a resection margin necessarily implies that surgery has been performed to achieve a 'resection margin' that can be treated.

US 2002/0094339 A1, U.S. Pat. Nos. 6,565,870 B1 and 6,139,845 all teach treating tumors, cancers and disorders with a botulinum toxin. The toxin is injected directly into the diseased tissue to exert its effect in inhibiting exocytosis.

Limitations of Prior Art

The prior art relies on the delivery of botulinum toxin directly into the cancer cells or to their immediate local vicinity to achieve an effect on the cancer cells. There are several substantial shortcomings of these methods which, if employed, may cause significant negative or adverse side effects to the treated tissue or its surroundings.

The first limitation of the prior art relates to the cholinergic innervation of cancer. The scientific literature is replete with reports that cancers are cholinergically innervated and that blocking this cholinergic innervation (with botulinum toxin) may reduce the ability of the cancer cell to divide, spread or invade locally. However, it is also clear that some cancers have the opposite effect by cholinergic stimulation, and that blocking this cholinergic innervation (with botulinum toxin) may actually enhance the ability of the cancer cell to divide, spread or invade locally, In fact, there are conflicting scientific reports that the same type of cancer (lung) may be stimulated or inhibited by cholinergic stimulation. When one considers the well-known fact that cancers are not a homogeneous population of cells but are usually a heterogeneous mixture, or that cancer cells are capable of modifying their responses, it becomes clear that blocking cholinergic innervation of a cancer may be good for some parts of a cancer, but bad for other parts. Alternatively a cancer that shrinks today from blocking cholinergic innervation may adapt and become stimulated by cholinergic innervation tomorrow.

A second significant limitation of the prior art relates to the fundamental concept of getting botulinum toxin into a cancer cell, where a cell's entire capacity to undergo exocytosis can be affected. US 2005/0031648 teaches that the substrate for a botulinum toxin is not restricted to neuronal cells which release acetylcholine, rather the substrates are "ubiquitously involved in membrane-membrane fusion events" and evidence points to "a universal mechanism for membrane fusion events" (para 0103). Once the toxin has been internalized into the affected cell, it acts in the known manner, as an endoprotease upon its respective secretory vessel-membrane docking protein (para 187). Furthermore, "as the concentration is raised, non-cholinergic sympathetic neurons, chromaffin cells and other cell types can take up a botulinum toxin and show reduced exocytosis" (para 191). Again, the goal is to reduce the excessive secretions from some cancerous cell by interfering with exocytosis, as also indicated in US 2002/0094339 A1, U.S. Pat. Nos. 6,139,845 and 6,565,870.

One fundamental problem of delivering the toxin into the cancer cell or diseased tissue's cell to interfere with exocytosis is that exocytosis within cancer cells is an absolute necessity to help kill cancer cells. Any attempt to globally eliminate or reduce exocytosis could certainly be hazardous, since all cells (including cancer cells) routinely undergo processing and presentation of molecules to their surface through exocytosis which serve to signal to the body's immune system whether a cell is cancerous or normal. Depending on the type of molecule presented to its surface, a cell may be killed by the immune system if it is considered 'cancerous' or protected if considered normal or 'self'. The process of cell signaling is dependent on an intact process of exocytosis. If these so-called tumor associated antigens are eliminated from the surface of a cancer cell by globally inhibiting exocytosis from within a cancer cell, the immune system will be less likely, if at all, to destroy the foreign cancer cell. Injecting directly into a cancer cell would further increase significant negative or adverse side effects of the treated tissue.

Thirdly, it has been taught that non-neuronal cells are less sensitive to botulinum toxin (US 2005/0031648 at para 191) and that, "as the toxin concentration is raised, non-cholinergic sympathetic neurons, chromaffin cells and other cell types can take up a botulinum toxin and show reduced exocytosis." It is well known to one skilled in the art that injections of higher concentrations of toxin are associated with a higher incidence of local side effects, because of spread to surrounding muscles and inadvertent muscle paralysis. Therefore, a high dose or concentration of toxin that is required to enter non-neuronal cells may cause excessive spread from the target area and cause affect not only the cancer cells, but also a significant area of surrounding tissue causing unacceptable side effects.

Fourth, there are other practical limitations of directly injecting a cancer or its vicinity with any substance, including botulinum. By directly injecting a cancer, one must insert a needle directly into to cancer and inject under pressure the desired substance. The needle may pass into then through the cancerous tissue and possibly seed cancerous cells into an area that did not contain cancerous cells in the first place. Even if the needle does not pass through the cancer, the pressure effect of the injectate may force or push cancerous cells into the surrounding normal tissue or into the thin walled lymphatics or blood vessels within or in the vicinity of the cancer, causing a higher chance of significant negative or adverse side effects, namely regional or distant metastases. For example, it is well known that one may bleed temporarily when a needle is stuck into the skin or gum following a dental visit. When this needle is entering a cancer, one must consider that the blood vessels have been broken and, at the microscopic level, cancer cells may have entered the circulation.

Fifth, patent application WO 2005/030248 describes a method of reducing actin filament association by getting botulinum toxin into cancer cells. Although it is taught that this may prevent cancer cells from contracting and migrating, it may also lead to loss of adhesion of malignant cells and result in increased distant spread.

Accordingly, there is a need for an effective method of treating a cancer using a neurotoxin. There is also a need for using a neurotoxin to treat other conditions.

OBJECTS OF THE INVENTION

It is an object to the present invention to treat cancer using a neurotoxin.

It is an object of the invention to treat a symptom of cancer using a neurotoxin.

It is a further object of the present invention to prevent metastasis of neoplasms using a neurotoxin.

It is a yet further object of the present invention to apply the neurotoxin around the cancer.

It is an even further object of the present invention to apply the neurotoxin around the cancer such that the neurotoxin surrounds the periphery of the cancer.

It is an additional object to the present invention to use the neurotoxin Botulinum.

Yet another object of the invention is to apply the neurotoxin by injection.

It is an additional object of the invention to positively modulate the immune system, both humoral and or cellular.

It is an additional object of the invention to treat an autoimmune disease, fungal disease, viral disease, viral-mediated disease, or immunodeficiency or immunodeficient state.

SUMMARY OF THE INVENTION

The present invention provides a method of treating a cancer using a neurotoxin, preferably Botulinum toxin. The application of a neurotoxin around a cancer acts to decrease the squeezing effect of contractile cells on the spread of cancer through tissue and through tubules draining the cancer. The application also paralyzes the lymphatic muscle that squeezes cancer cells and lymph through the circulation. The application also positively modulates the immune system to enhance cellular or humoral mechanisms against the cancer. Following administration of botulinum toxin around a cancer, regional, and distant spread is reduced or eliminated. In a preferred embodiment, the neurotoxin is administered in such a way that it surrounds the cancer.

The invention accomplishes a method of inhibiting growth, invasion or spread of cancer cells using a neurotoxin. The method is easily adapted to cancer therapy at the time a cancer is initially diagnosed and could significantly improve the outcome of a patient diagnosed with cancer by reducing local, regional or distant spread. The technique could be used for patients undergoing either surgery, radiation therapy, chemotherapy or other forms of treatment for the diagnosed cancer. It can also be used as a sole modality of therapy.

The neurotoxin is preferably applied by injection. In a preferred embodiment, the neurotoxin is injected into the tumor in a sufficient quantity that it surrounds the periphery of the tumor. This latter method can be accomplished by a single injection or multiple injections. Of course, if accessible, it is understood that the neurotoxin could be applied topically to the periphery of the tumor. Also, in for example the case of lung cancer, the neurotoxin can be applied by aerosol. In addition, it is understood that the neurotoxin can be applied around a metastasis to induce the desired effects.

The neurotoxin, in a preferred embodiment, is injected also into local, regional or distant lymphoid tissue which can be done with visual (eye or scope) or radiographic guidance such as a CAT scan or ultrasound guidance.

The therapy is applicable, but not limited to the following sites. Regional muscles, even at the microscopic level, surround almost every bodily location and therefore, most body sites are amenable to neurotoxin treatment. Regarding lymphoid injection sites, one would inject the surrounding regional lymphoid tissues (if the cancer were present on a mucosal surface), and/or the regional nodal basins. Distant injections into the thymus, spleen, bone marrow or other hematopoietic sites can be performed by injection as well.

The therapy is also applicable to other diseases characterized by a poor cellular or humoral response. Botulinum toxin would be injected locally into areas characterized by a poor cellular or humoral response, such as into the pancreas in the patient with insulin dependent diabetes, into the mucosa of the nose in a patient with fungal sinusitis, into the wart in the patient with veruca vulgaris or into a wound in the patient with a non-healing wound, or into the thymus, spleen or bone marrow in the case of a patient with immunodeficiency.

DETAILED DESCRIPTION OF THE INVENTION

The present invention is distinct in that it treats normal, non-diseased, non-cancerous cells in order to treat a cancer. Treatment means to reduce, prevent or eliminate cancer cells or the spread of cancer cells or the symptoms of cancer in the local, regional or systemic circulation. The present invention treats cancer, metastases and precancerous conditions, as well as viral mediated growths or disorders, chronic infections and immune-mediated disorders by distantly injecting botulinum toxin. Botulinum toxin injections will reduce or eliminate the symptoms of a cancer, metastasis or metastases, precancerous conditions, viral mediated growths or disorders, chronic infections and immune-mediated disorders. The preferable disorder is cancer.

For the present application, the terms neoplasm and cancer are used interchangeably, and both terms are understood to include precancerous conditions.

Unlike prior art that teaches how to treat a diseased tissue such as a cancer with a neurotoxin, the present method relies not on the direct effect of botulinum toxin on a cancer or its innervation, but rather on the well known affinity of botulinum toxin for muscle, specifically the muscle that surrounds cancer. Because of the extremely high affinity of the toxin for muscle, this method poses a significant advantage over prior art in that much smaller doses of toxin may be used to elicit an effect. The smaller doses will result in fewer dose-related side effects such as the inadvertent spread of toxin through the tissues to neighboring structures, and resistance to future botulinum injections. There will be limited spread to the vicinity of the cancer or directly to the cancer since the toxin rapidly binds to the neuromuscular junction in the injection vicinity. Furthermore, even if the toxin were to spread to the cancer or its vicinity, the small doses would not exert an effect on the diseased tissue which have little affinity for the toxin substrate. In fact, the doses utilized in the preferred embodiment are already FDA approved for use in other neuromuscular conditions that are treated with botulinum toxin.

Another distinct advantage of the present invention is that it is a 'no-touch' method that intentionally avoids the cancer or its vicinity. Since the application is not by needle injection into or near a cancer, there is no risk of inadvertently seeding cancer cells into surrounding tissue, and there is no risk of creating a local pressure gradient that could push cancer cells into surrounding tissue or into penetrated blood vessels or lymphatic channels.

The invention is also novel in that it distantly modulates the immune system to enhance immunologic activity against cancer, metastases, precancerous conditions, viral mediated growths or disorders, chronic infections and immune-mediated disorders. A distant injection into a lymph node, regional lymphatic tissue or immunologic producing or enhancing structure (such as the spleen or thymus) may enhance lymphocytic or humoral responses against the condition.

In treating non-cancerous conditions such as viral infections, viral diseases, viral-induced growths, autoimmune diseases, multiple sclerosis, chronic wounds, chronic infections, bone infections, rheumatoid arthritis, myasthenia gravis, HIV, chronic fatigue syndrome and hepatitis the neurotoxin can be administered in the same way, and using the same dosages, as it is administered to treat neoplasms. That is, the neurotoxin can be applied to the area around the diseased or affected tissue as well as optionally to proximate and/or distal lymph nodes, the thymus, the spleen and/or the bone marrow. There are, however, several other optional methods of applying neurotoxin to treat these non-cancerous conditions.

For example, where a specific area of diseased or affected tissue can be identified, the neurotoxin can be injected directly into the diseased or affected tissue. Thus, if a patient is suffering from type 1 diabetes, neurotoxin can be injected directly into the pancreas. For multiple sclerosis, the neurotoxin is injected intrathecally. For chronic infections, viral infections, viral diseases and viral induced growths, the neurotoxin can be directly injected into the affected tissues. For hepatitis, neurotoxin can be injected directly into the liver. For Sjogren's syndrome, the neurotoxin can be injected directly into the moisture producing glands.

For treating an autoimmune disease that affects blood vessels, the neurotoxin can be applied to the tissues surrounding the blood vessels, allowing diffusion of the neurotoxin into the blood vessels.

To treat the above conditions, the neurotoxin can also be applied to the area surrounding the affected tissue. Moreover, the neurotoxin can further be injected into the proximal lymph nodes, the distal lymph nodes, the thymus and/or the spleen.

Some conditions, such as chronic fatigue, HIV and AIDS, are systematic and do not involve a single organ system or tissue. In that event, the condition is treated by injecting the thymus, spleen or bone marrow. Of course, the lymph nodes can also be injected.

For injecting an organ or a tissue, especially one which cannot be seen visually, the needle can be guided into place using conventional techniques. These techniques include, but are not limited to, palpitation, ultra sound guidance, CAT scan guidance and X-ray guidance.

The preferred neurotoxin is botulinum toxin type A. Dosages used are the same as those used for treating neoplasms.

Botulinum Toxin

The anaerobic, gram positive bacterium Clostridium botulinum produces a potent polypeptide neurotoxin, botulinum toxin, which may cause a neuro-paralysis in humans. The neuro-paralysis is commonly referred to as botulism. Clostridium botulinum bacterium is commonly found in soil and will grow in improperly sterilized food containers. Signs and symptoms of botulism normally occur in humans within 18 to 36 hours after consuming foods containing a culture of Clostridium botulinum. It is thought that the botulinum toxin can pass through the lining of the gut and effect the peripheral motor neurons. The symptoms of botulinum begin with difficulty walking, swallowing, and speaking and progress to paralysis of the respiratory muscles resulting in death.

The Use of Botulinum Toxin for Cancer Therapy:

The Cholinergic Influence on Cancer:

1) Some Cancer Cells are Activated by Cholinergic Stimulation

Several forms of cancer have been demonstrated to have muscarinic cholinergic receptors that are capable of inducing mitogenesis in cells capable of undergoing cell proliferation.

Prostate: Carbachol, an acetylcholine analog, stimulates DNA synthesis in prostate cancer cells (Rayford W. et al. Muscarinic Cholinergic Receptors Promote Growth of Human Prostate Cancer Cells. The Prostate 30, 1997, abstract) and stimulation of the M3 muscarinic receptor on prostate cancer cells stimulates proliferation (Luthin G R, et al. Role of m1 receptor-G protein coupling in cell proliferation in the prostate. Life Sci 60, 1997, abstract).

Colon: M3 receptors are overexpressed in human colon cancer compared with normal colon tissue, and activation of this receptor may contribute to the malignant progression of human colon carcinoma (Yang W, et al. Cholinergic receptor up-regulates COX-2 expression and prostaglandin E2 production in colon cancer cells. Carcinogensis 21, 2000, pg. 1789). Ukegawa (Ukegawa J, et al. Growth-promoting effect of muscarinic acetylcholine receptors in colon cancer cells. J Cancer Res Clin Oncol 129, 2003, abstract) recently demonstrated that activation of the M3 muscarinic cholinergic receptor has a growth promoting effect on colon cancer cell lines.

Lung: Stimulation of the muscarinic acetylcholine receptor expressed on small cell lung carcinoma stimulates cell growth (Song P, et al. Acetylcholine is synthesized by and acts as an autocrine growth factor for small cell lung carcinoma Cancer Res 63, 2003, abstract). It has been demonstrated that small cell lung cancer cell lines synthesize and secrete acetylcholine to act as an autocrine growth factor (Song, P. et al. Acetylcholine is synthesized by and acts as an autocrine growth factor for small cell lung carcinoma. Cancer Res 63, 2003, abstract). Human mesothelioma cell growth is modulated by the cholinergic nervous system, and agonists have a proliferative effect (Trombino S, et al. Alpha-7 nicotinic acetylcholine receptors affect growth regulation of human mesothelioma cells: Role of Mitogen-activated Protein Kinase Pathway. Cancer Res 64, 2004, pg. 135). Interestingly, Williams found that stimulation of muscarinic receptors enhanced cell-cell adhesion in small cell lung carcinoma.

Breast: Murine mammary adenocarcinoma cell lines undergo proliferation in response to carbachol that is mediated via M3 receptor activation (Espanol A, et al. Different muscarinic receptors are involved in the proliferation of murine mammary adenocarcinoma cell lines. Int J Mol Med 13, 2004, abstract).

Brain: Carbachol stimulation caused a dose and time dependent increase in proliferation of human astrocytoma cells (Guizetti M, et al. Acetylcholine as a mitogen: muscarinic receptor-mediated proliferation of rat astrocytes and human astrocytoma cells. Eur J Pharmacol 297, 1996, abstract).

Melanoma: Primary and metastatic melanoma cells reexpress muscarinic cholinergic receptors, which, when stimulated, cause cellular movements and contractions (Sailer M, et al. Induction of cellular contractions in the human melanoma cell line SK-mel 28 after muscarinic cholinergic stimulation. Anat Embryol 201:27-37, 2000). It has been hypothesized that such stimulation may be responsible for invasive growth of melanoma, and also that a cholinergic autocrine loop may be established in melanoma. In a histochemical study, muscarinic acetylcholine receptors were found to be highest in the periphery of the melanoma, at its junction with normal tissue (Lammerding-Koppel M, et al. Immunohistochemical localization of muscarinic acetylcholine receptors in primary and metastatic malignant melanomas. J Cut Pathol 25, 1997, abstract).

Lymphocytes: Human leukemic T-cells have the potential to synthesize and release acetylcholine which may play a role in regulating t-cell dependent immune responses (Fjuii T, et al. Localization and synthesis of acetylcholine in human leukemic T cell lines. J. Neurosci Rest 44, 1996, abstract).

Ovarian: In ovarian cancer, not only did a large percentage of ovarian cancers express muscarinic receptors, but such expression was associated with a reduced probability of survival (Oppitz M, et al. Muscarinic receptors in cell lines from ovarian carcinoma: negative correlation with survival of patients. Gynecol Oncol 85, 2002, abstract).

Head and Neck: Carbachol treatment of head and neck squamous cell carcinoma activates the epidermal growth factor receptor (EGFR) which plays a direct role in the regulation of the migratory behavior of head and neck cancer cells (Geschwind A, et al. Lysophosphatidic Acid-induced Squamous Cell Carcinoma Cell Proliferation and Motility Involves Epidermal Growth Factor Receptor Signal Transduction. Cancer Res 62, 2002 p. 6335). In fact, EGFR activation leads to head and neck squamous cell carcinoma invasion (Geschwind A, et al. Lysophosphatidic Acid-induced Squamous Cell Carcinoma Cell Proliferation and Motility Involves Epidermal Growth Factor Receptor Signal Transduction. Cancer Res 62, 2002 p. 6335). Furthermore, the effect may be mediated by amphiregulin. In squamous cell carcinoma cells, carbachol specifically results in the release of amphiregulin (Geschwind A, et al. TACE cleavage of proamphiregulin regulates GPCR-induced Proliferation and motility of cancer cells. EMBO J 22, 2003, abstract). Amphiregulin is known to release metalloprotease enzymes in malignant cell lines and such release may be associated with local invasiveness and metastasis (Lui, Z, et al. Regulation of matrix metalloprotease activity in malignant mesothelioma cell lines by growth factors. Thorax 58:198-203, 2003)). In non-small cell lung cancer, amphiregulin can inhibit apoptosis (Hurbin A, et al. Inhibition of apoptosis by amphiregulin via an insulin-like growth factor-1 receptor-dependent pathway in non-small cell lung cancer cell lines. Ann NY Acad Sci 1010, 2003, abstract).

2) Some Cancer Cells are Inhibited by Cholinergic Activation

It has also been demonstrated that in small cell lung carcinoma (SCLC), activation of M3 muscarinic acetylcholine receptors causes decreased cell proliferation, increased E-cadherin-mediated cell-cell adhesion, and increased Beta 1 integrin-mediated cell-substrate adhesion (Williams, muscarinic signaling in carcinoma cells, Life Sciences 72 (2003), 2173-2182). Increased cell-cell adhesion and cell-substrate adhesion would produce decreased metastases.

Cholinergic stimulation of pre-neoplastic cell line (NIH3T3) can cause both inhibitory and stimulatory growth mechanisms as well (Nicke, B. et al. Muscarinic Cholinergic Receptors activate both inhibitory and stimulatory growth mechanisms in NIH3T3 cells, J. Biol. Chem. 1999, vol. 274, no. 31, pp. 21701-21706).

3) Some Cancers are Parasympathetically Innervated

In 2001, the first report was published that demonstrated that neoplastic tissue is innervated (Seifert P, et al. Tumors may be innervated. Virchows Arch 438, 2001, abstract). In 2002, Seifert reported that papillary bladder carcinomas were parasympathetically innervated (Seifert P, et al. Nerve fibers in tumors of the human urinary bladder. Virchows Arch 440: 291-297, 2002).

4) Angiogenesis is Stimulated by Acetylcholine

Angiogenesis consists of sequential processes emanating from microvascular endothelial cells. The parasympathetic nervous system has been shown to positively modulate neovascularization by stimulating M3 receptors and prostaglandin E2 liberation (Heeschen C, et al. A Novel Angiogenis Pathway Mediated by Non-Neuronal Nicotinic Acetylcholine Receptors. Journal of Clin Invest 110:527-536, 2002).

5) To Block the 'Universal Docking Mechanism' in Cancer Cells

It has been theorized and demonstrated that botulinum toxin acts by inhibiting a 'universal docking mechanism' within all cells by interfering with the formation of a SNARE complex between two membranes that will fuse and undergo exocytosis. This concept has been applied to the treatment of cancer, by theorizing that such as effect will help reduce a cancer cells activity (US 2005/0031648 A1) or reduce actin filament association and therefore reduce a cancer cells movement (WO 2005/030248).

There are significant practical and safety limitations to this approach which have been detailed above. First botulinum toxin does not enter non-neuronal cells unless the cell has been permeabilized (in vitro only), a transport vehicle has been bound (in vitro only), or if a significantly higher dose of toxin has been injected. Higher does of botulinum injections may cause greater inadvertent spread with subsequent paralysis of neighboring structures, increased resistance to future injections. Other practical limitations of injecting a cancer with botulinum toxin have also been detailed above, but include possible seeding of cancer cells to neighboring normal tissue, penetration of lymphatic vessels or blood vessels within the cancer causing a higher likelihood of spread, or producing a pressurized bolus effect on the cancer which may lead to spread.

CONCLUSION: The significant uncertainty of a cancer's response to botulinum toxin would prohibit its direct use in cancerous tissue. It is concluded that one should avoid introducing botulinum toxin into a cancer.

6) Distant Injections of Botulinum Toxin Will Reduce Metastases and Provide Safer Local Therapy of Cancer To cure cancer, it is paramount to control not only local disease, but to control and treat distant spread called metastases. Metastases can be regional (within the neighboring lymphatic structures) or distant (far away from the primary site). Metastases generally occur by lymphatic or hematogenous spread. Spread through lymphatic channels is facilitated primarily through the contraction of skeletal or smooth muscle fibers surrounding the lymphatic network. It is well known that botulinum toxin has the absolute strongest affinity for skeletal muscle fibers and weakens or paralyzes them upon exposure. Minute amounts of toxin are needed to accomplish this and the range of doses that is needed to accomplish this is well-established for other non-cancerous conditions. Furthermore, it is well-established that the immune system is of paramount importance in eliminating cancerous cells both at the primary site and within the circulation.

The present invention accomplishes but is not limited to the treatment of cancer by treating cancer at the primary site by enhancing the immune response to malignant cells, preventing the spread by weakening regional contractile forces in and around lymphatic and bleed vessel structures, and treating cancerous cells within the circulation. The present invention is distinct from prior art in that the toxin is not injected near cancerous cells. The present invention poses several advantages over prior art including the need to use smaller doses, the avoidance of direct injections into the cancer, the avoidance of the uncertain responses of a cancer cell to botulinum toxin.

A review of relevant anatomy follows:

1) Localization of Lymphatic Tissue

Besides blood vessels, the human body has a system of channels that collects fluid from the tissue spaces and returns it to the blood. This fluid is called lymph, and in contrast to blood, it circulates in only one direction, toward the heart.

The lymphatic capillaries originate as blind-ended, thin walled vessels. They consist of thin walled endothelium. These thin walled vessels ultimately converge and end up as two main trunks, the thoracic duct and the right lymphatic duct. These enter into the junction of the left internal jugular vein and the left subclavian vein, and into the confluence of the right subclavian vein and the right internal jugular vein. Interposed in the path of the lymphatic vessels are lymph nodes. The larger lymphatic vessels have a smooth muscle layer that helps propel lymph flow through the channels and unidirectional lymph flow occurs secondary to the presence of many one-way valves.

The lymphatic ducts of large size (thoracic and right lymphatic ducts) have a reinforced smooth muscle layer in the middle, in which the muscles are oriented longitudinally and circularly. They contain vasa vasorum and a rich neural network (Junqueira L, Basic Histology, 1986, Lange Medical Publications, page 269)

Lymphoid Tissue

The spleen, thymus and bone marrow are also considered lymphoid tissue. These lymphoid organs are classified as either being central or peripheral and encapsulated (e.g. spleen or lymph nodes) or unencapsulated (e.g. tonsils, peyers patches in the intestine, lymphoid nodules found throughout the mucosa of the alimentary, respiratory, urinary and reproductive tract). (Junqueira L, Basic Histology, 1986, Lange Medical Publications, page 269)

In general, lymphoid cells begin in a 'central' lymphoid organ where lymphoid precursors undergo antigen-independent proliferation and acquire surface antigens that mark them as committed to either the cellular or humoral immune response. The thymus is the central organ where lymphocytes take on the capacity to participate in the cellular immune response (T cells). Cells migrate through the blood from the bone marrow to the thymus, where they proliferate, giving rise to T cells These lymphocytes are responsible for cell-mediated immune reactions. The bone marrow is where progenitor cells differentiate into humoral immune cells (B-cells) which ultimately become plasma cells and secrete immunoglobulins and provide the humoral immune response. Lymphocytes leave the central lymphoid organs and populate specific regions of "peripheral" lymphoid organs, such as lymph nodes, spleen, peyer's patches and diffuse unencapsulated lymphoid tissue in the mucosa of the digestive, respiratory, urinary and reproductive tracts (Junqueira L, Basic Histology, 1986, Lange Medical Publications, page 269).

Spleen: The spleen is the largest lymphatic organ in the circulatory system. The spleen is a site of formation of activated lymphocytes. It serves to filter and modify the blood.

Thymus: The thymus is a central lymphoid organ located in the mediastinum. There is intense lymphocytic proliferation that occurs in the thymus during embryonic through pre-pubertal development. This is where cells proliferate that become T lymphocytes, the cells responsible for cell-mediated immunity. From the thymus, these T cells leave through blood vessels to populate the peripheral lymphoid organs, especially lymph nodes and the spleen.

Bone Marrow: The bone marrow is also a central organ, but it gives rise to B cells, which ultimately differentiate into plasma cells and secrete antibodies (the humoral immune system). After differentiation, the B cells travel to lymph nodes, the spleen and especially Peyer's patches in the intestine (Junqueira, supra, page 312).

Lymph Nodes: Lymph nodes are encapsulated areas of peripheral lymphoid tissue. They are distributed throughout the body, always along the course of lymphoid vessels, which carry lymph into the thoracic and lymphatic ducts (Junqueira, supra, page 313). Lymph nodes are aggregated in particular sites such as the neck, axillae, groins and para-aortic region. The precise location of lymph nodes is well-known. See, e.g., Le, UAMS Department of Anatomy—Lymphatics Tables (Jul. 16, 2005), which is incorporated herein by reference in its entirety.

Lymph enters the lymph nodes through the afferent lymphatic channel and exits through the efferent channel. Flow is unidirectional. As lymph flows through the sinuses, 99% or more of the antigens or other debris are removed by the phagocytic activity of the macrophages within the node. Some of the material is trapped on the surface of dendritic cells, which is then exposed on the surface of the dendritic cell and recognized and acted upon by immunocompetent lymphocytes. The parenchyma of a lymph node has three general regions, the cortex, paracortex and medulla.

In the cortex, if a B cell recognizes an antigen (and sometimes with the help of T cells) the B cell may become activated and synthesize antibodies which are released into the lymph fluid then into the circulation. Activated B cells remain within the lymph node. Unstimulated B cells pass out of the lymph node and return to the general circulation.

T cells remain predominantly in the paracortex region of the lymph node. Activated T cells pass into the circulation to reach the peripheral site. Other cell types, predominantly antigen presenting cells, reside in the paracortical region of the lymph node.

The medulla is rich in plasma cells which produce further antibodies, and macrophages.

Unencapsulated tissue: Unencapsulated lymphoid tissue can be found mainly in the loose connective tissue of many organs, mainly in the lamina propria of the digestive tract, upper respiratory tract and urinary passages (Junqueira, supra, page 323). The palatine, lingual and pharyngeal tonsils are another main site of unencapsulated lymphoid tissue. This so-called mucosa-associated lymphoid tissue (MALT) includes gut-associated lymphoid tissue (GALT), bronchial/tracheal-associated lymphoid tissue (BALT), nose-associated lymphoid tissue (NALT), and vulvovaginal-associated lymphoid tissue (VALT). Additional MALT exists within the accessory organs of the digestive tract, predominantly the parotid gland.

MALT may consist of a collection of lymphoid cells or may include small solitary lymph nodes. Stimulation of B lymphocytes leads to the production of immunoglobulin A (IgA) and IgM within the peyers patches. Additionally, epithelial surfaces contain M cells which are specialized cells that absorb, transport and present antigens to subepithelial lymphoid cells, such as CD4 type 1 helper cells, antigen presenting cells and memory cells.

A more specific discussion of lymphocytes will follow below, but generally, lymphocytes contain antigen receptors that trigger differentiation. In peripheral organs, lymphocytes interact with appropriate antigens, enlarge then divide. Some become effector cells, and others become memory cells that are responsible for the secondary immune response. To generate an immune response and for effector cells to be generated, antigen must be delivered to them. This is the job of antigen presenting cells which include dendritic cells, macrophages and Langhans cells in the epidermis.

Effector cells can be activated B- or T-cells. B-cell effector cells are plasma cells that secrete immunoglobulins into the surrounding connective tissues. T-cell effector cells are of several types and include helper T cells, suppressor T cells and cytotoxic T cells. Cells attacked include tumor and viral-infected cells. T cells and macrophages secrete lymphokines that regulate the proliferation of both B and T cells.

Lymphatic Flow

The lymphatic system is found in almost all organs except the central nervous system and the bone marrow. The lymphatic circulation is aided by the action of external forces such as the contraction of surrounding skeletal muscle on their walls. (Junqueira, supra, page 269). These forces cause transportation along lymphatic channels. Contraction of smooth muscle in the walls of the larger lymphatic vessels also helps propel lymph. The transport of lymph depends on active and passive driving forces. The active driving force resulting from intrinsic pump activity in some lymph vessels plays an important role in the propulsion of lymph flow (Hosaka K, et al. Am J Physiol Heart Circ Physiol 284, 2003, abstract) There is myogenic tone in lymph channels. It has been demonstrated that the Rho kinase pathway (which is inhibited by botulinum toxin) helps regulate the lymph pump activity (Hosaka, supra). In fact, it has been demonstrated that lymph vessels are capable of regulating flow through intrinsic mechanisms (Ferguson MK, et al. Lymphology 27(2), 1994 abstract and, Muthuchamy M, et al. Molecular and Functional analyses of the contractile apparatus in lymphatic muscle. FASEB J 17, 2003, abstract). Larger lymphatic ducts contain smooth muscle and a rich neural network (Junqueira, supra, page 269).

Several factors aid the flow of lymph fluid from tissue spaces to lymph nodes and finally to the venous bloodstream: 1) "Filtration pressure" in tissue spaces, generated by filtration of fluid under pressure from the haemal capillaries; 2) Contraction of neighboring muscles compresses the lymph vessels, moving lymph in the direction determined by the arrangement of valves; 3) Pulsation of adjacent arteries; 4) Respiratory movements and the low blood pressure in the brachiocephalic vein during inspiration; 5) Smooth muscle in the walls of lymphatic trunks is most marked proximal to their valves. Pulsatile contractions in the thoracic duct are known to occur also.

2) Lymphatics, Cancer and Metastases

Cancers spread by the lymphatic and hematogenous circulations. The lymphatic and vascular systems have numerous connections, and tumor cells may pass from one system to another. During invasion, cancer cells may enter the thin walled small lymphatic vessels and be passively transported in the lymph. Tumor emboli may be trapped in the first lymph node or nodes ("regional" nodes) encountered on their route, or they may bypass regional nodes and be transported to distant nodal groups ("skip metastases"). Recent advances in mapping of the lymphatics draining cancers have allowed surgeons to identify the lymph node draining the tumor site (the "sentinel lymph node").

Each body region usually drains into a select lymph node or group of nodes, which have been detailed precisely in anatomic studies and is known in the art. See, e.g., UAMS Department of Anatomy-Lymphatic Tables, supra, previously incorporated into this application in its entirety.

Certain factors may facilitate the entry of cancer cells into the circulation and lead to metastases. Physical pressure within a cancer environment may lead to dissemination of malignant cells both locally and distantly (Targarona E M, et al. World J Surg 22, 57-58, 1998, and Lacy A M, et al. Surg Endosc 1988, 12:1040-1041). Also, a 'no-touch' technique of surgical excision has been advocated to reduce the effect of 'massaging' cancer cells into the circulation through manipulation. In this technique it is important to ligate the blood supply of the tumor before attempting mobilization of the tumor. These various clinical techniques emphasize the need to minimize the direct physical manipulation of a cancer to reduce the chance of facilitating spread.

Clinically, it has been demonstrated (Hiroto M, et al. Journal of Pancreas 6(2):143-151, 2005), that all lymphatic fluid samples squeezed from resected cancerous pancreatic tissue were positive for CEA messenger RNA, urging the need to minimize the spread of draining lymphatic fluid from a cancer.

3) Botulinum Toxin Will Weaken Lymphatic Transit

The effect of botulinum toxin on skeletal muscle is well-known. In fact, it is the basis of therapy for conditions such as strabismus, dystonias and other spastic muscle conditions. The FDA has granted approval of botulinum therapy for strabismus, blepharospasm, cervical dystonias and others. The range of doses needed to paralyze various muscles in the body is well-established.

A regional injection of botulinum toxin around a cancer will exploit the well-known binding affinity of botulinum for muscle. Skeletal muscle, smooth muscle, lymphatic muscle, blood vessel muscle and pericyte muscle will be the non-limiting target of this invention. The paralysis of surrounding skeletal or smooth muscle will limit the contractile extrinsic forces on lymphatic structures that normally facilitate flow of lymph through lymphatic channels. The intrinsic muscles within lymphatic tubules will be paralyzed or weakened by botulinum therapy. The smooth muscle wall of blood vessels will be weakened as well (?JERRY-add this about blood vessels?).

Alternative Method of Treating Cancer with Distant Botulinum Toxin Injections:

A second method of treating cancer with distant botulinum injections relates to the ability to modify the immune system and enhance the response to cancer using botulinum toxin therapy. The basis for this relates to the cholinergic innervation of the immune system and, therefore, also relates to the treatment of other non-cancerous conditions that exist because of a poor or weakened immune response. With respect to cancer therapy, it is again important to avoid introducing the toxin to the cancer cells since exocytosis within cancer cells is paramount to presenting the appropriate antigens for immune recognition and destruction by the immune system. In fact, distant injections of toxin into lymphatic organs (lymph nodes, lymph tissue) are preferred.

1) Normal Immune Response to Cancer

Antitumor immune responses can be innate (natural) or acquired (adaptive). Innate immunity is mediated by cells or soluble factors which naturally exist in tissues of body fluids and can interfere with tumor growth (Whiteside T L. J. Allergy Clin Immunol 2003; 111, S677-86). The hematopoietic cells included are macrophages, granulocytes, natural killer cells, non-MHC-restricted T cells abd gamma/delta T cells. Also, natural antibodies directed at the surface components of tumor cells, complement components, C reactive protein, serum amyloid protein, mannose-binding protein are also included (Whiteside, supra). Adaptive immunity is mediated by T cells which recognize tumor-derived peptides bound to self-MHC molecules expressed on antigen presenting cells (APC). These cells include cytolytic effector cells, which are CD8+ and MHC class I restricted, but also helper CD4+ T cells (Whiteside, supra).

Immune responses to malignant cells can be categorized as local/regional or systemic. Local responses include tumor infiltrating leukocytes (TIL). Systemic responses exist and are measured by the peripheral circulation delayed type hypersensitivity (DTH) in patients with cancer.

2) Immune Cells in the Tumor Microenvironment

Whiteside, supra, reviews the tumor microenvironment. TIL are frequently found in tumors. These cells may include cells mediating innate and adaptive immunity. A variety of soluble products such as cytokines and antibodies may be released in the microenvironment as well. Theoretically these products combined with direct interactions of infiltrating effector cells should result in cancer cell death, but because of the mechanisms outlined above, this often does not occur.

T cells are found in the greatest abundance of all mononuclear tumor infiltrates. It has been demonstrated that T cells in the tumor microenvironment include CD4+ (helper) and CD8+ (suppressor) cells. They have been demonstrated to be dysfunctional in cancer patients and the magnitude of their dysfunction may be related to the prognosis and survival in patients with cancer. Traditionally, the protective T cell response to tumors has been ascribed to CD8 T lymphocytes with cytotoxic activity, which are restricted by MHC Class I molecules, but recently CD4 cells have been considered to play an anti-tumor role (Gerloni M, et al. Springer Seminars in Immunopathology, Springer-Verlag 2005, 1-15). In general, both cellular and antibody-mediated responses are used for anti-tumor responses. Antibody responses are best suited for extracellular pathogens and antigens, and cell-mediated responses are best suited for intracellular pathogens and tumor cells (Gerloni, supra). Since tumor antigens are always endogenous antigens, tumors may be better suited for destruction by cell-mediated immunity. Furthermore, since tumors are MHC II negative, most efforts have focused on CD8 T lymphocytes, The role of CD4 lymphocytes has been demonstrated as well, since they help activate and expand CD8 lymphocytes as well. There are two subsets of CD4 lymphocytes, the T helper 1 (Th1) and Th2 cells. Th1 cells produce interleukin-2 (IL-2), IL-12 and interferon-gamma (INF-G) and Th2 produce IL-4 and IL-5. These cytokines affect B cells and help further influence the type of antibody response to antigen activation (Gerloni, supra. CD4 cells may help activate macrophages in draining lymph nodes or in tumor tissue.

Cell-cell cooperation may also exist among CD4 cells. Gerloni, supra, has demonstrated that a CD4 cell may activate and expand other CD4 cells as well.

The production and release to the cell membrane of cellular antigens is of paramount importance is tumor immunity and destruction. Both MHC class I and class II-restricted antigens are involved in the anti-tumor response. Most focus on tumor immunity has focused on the role of MHC class I restricted antigens but class II antigens are important as well. Class II antigens are tissue specific, shared among various types of tumors, true common tumor antigens and viral antigens that cause tumor transformation (such as Human Papilloma Virus or Epstein Barr Virus antigens).

Natural killer cells (NK) mediate innate immunity and are well equipped to lyse tumor cells. These cells are thought to facilitate dendritic cell/T cell interactions and drive the immune response to TAA. In general it is thought that these cells are not abundant in the tumor microenvironment but this may be because of the difficulty reliably identifying them. Also, NK cells are dependent upon Interleukin-2 (IL-2) for activation, which is generally deficient in human tumors. (Whiteside, supra. NK cells are also capable of responding to virus-infected cells. NK cells play a critical role in limiting viral infections as been provided by studies with herpes virus such as cytomegalovirus (CMV), herpes simplex virus (HSV) and Epstein-Barr virus (EBV) as well as human immunodeficiency virus (HIV) (Smyth M J, et al. Molec Immunol 42 (2005) 501-510). The effector functions of NK cells, including cytotoxicity and the capacity to produce a variety of cytokines (including INF-gamma) following activation which restricts tumor angiogenesis and stimulates adaptive immunity (Smyth, supra. Clinically, enhancement of NK cell function parallels clinical improvement in cancer patients (Lechin F, Clin Canc Research 2004, 10:8120).

B cells are also rare in most tumors except breast cancer and melanoma. The function of B cells is differentiation into antibody-producing plasma cells. In general, antibodies to TAA are found in the circulation of patients with cancer, and they are thought to be made from and secreted from tumor-draining lymph nodes, spleen or other lymphoid tissues. From there, IgG molecules are transported by plasma or lymph to tissue sites.

Dendritic cells (DC) are common in human cancers. These cells process and present TAA to naïve or memory T cells, thus play a crucial role in the generation of tumor-specific effector T cells. In patients with cancer, DC are sometimes dysfunctional. However, DC infiltrations into tumors have been associated with significantly prolonged patient survival and reduced incidence of recurrent or metastatic disease. Conversely, patients with lesions scarcely infiltrated with DC have a relatively poor prognosis.

Macrophages are also found in the tumors microenvironment and are called tumor associated macrophages (TAM). In tumors, TAM actually inhibit lymphocyte function including T cell proliferation and NK-mediated antitumor cytotoxicity.

3) Immune Suppression in the Tumor Microenvironment

As mentioned above, cancers can evade the immune system and thereby escape recognition. These include expression by tumors of poorly immunogenic antigens, defects in antigen processing, inadequate costimulatory interactions, production of immunosuppressive factors, or through the fact that immune cells are compromised in number and/or function (Hoffman T K, et al. Cancer Immunol Immunother (2004) 53:1055-1067)

4) Immune Effector Cells in the Circulation of Cancer Patients Just as the local microenvironment contains dysfunctional immunocytes, the peripheral blood lymphocytes contain function irregularities as well. Signaling abnormalities, functional impairments and apoptosis are seen in T cells, NK cells, macrophages and B cells in the peripheral circulation.

5) Local Immunotherapy and Cancer Response

The ability to modulate the local immune environment is important for cancer therapy. When low doses of natural IL-2 were injected around tumor-draining lymph nodes, 65% of patients had a complete, partial or minimal response (Feinmesser M et al. Eur Arch Otorhinolaryngol (2004) 261:359-368). Unfortunately, the effect was short-lived and multiple daily or weekly injection are required (Shibuya T Y, et al. Clin Canc Research 2004, 10:7088-7099). In other studies using peritumoral infiltration of lymphokine with or without regional infiltration into the lymph nodes, similar regression was noted (Feinmesser, supra).

The administration of bioactive suture, coated with INF-gamma, IL-2, have been shown to generate a prolonged Th1 response and stimulate the secretion of IL-12 and prolong the immune response (Shibuya T Y, et al. Clin Canc Research 2004, 10: 7088-7099). In this therapy the suture is considered a carrier for the bioactive products, and is placed using a 'Seldinger technique' whereby a needle with a trochar is introduced into the desired location and the suture is subsequently passed. Placement of the suture is invasive and the suture be kept long and attached to the skin surface, 'similar to a surgical drain' which may potentially lead to infection.

In effort to enhance local immune function, cytokine genes have been transduced into the patient's tumor cells. Again the underlying concept is to stimulate a vigorous immune response by enhancing local cytokine production. Pitfalls of this technique include the reliance on tumor cells to produce an effect, and the lack of adequate quantity and quality of patient tumor cells and the heterogeneous expression of the cytokine genes. Also the tumor cells must be irradiated prior to reintroduction into the patient (Steele T A, et al. PSEBM 2000, 23:118-127).

6) Immunotherapy Strategies

In general terms, there are two forms of immunotherapy, active and passive. Active immunotherapy refers to the induction of immune responses through application of immunogenic tumor antigens (such as peptides, proteins, tumor cells or tumor lysates), whereas passive immunization relies on the transfer of immune effector molecules or immune cells (Hoffman T K, et al. Cancer Immunol Immunother (2004) 53:1055-1067).

Active immunomodulators can be nonspecific or specific. An active, nonspecific immunomodulator may include local therapy with BCG, thymic extracts or OK-432 which attempt to induce an antitumor response. Such therapy however, has not demonstrated consistent survival benefits to cancer patient. Active, specific immunomodulation may include the administration dendritic cell-based vaccines or DNA-based vaccines. Such therapy is in its infancy and is usually reserved for recurrent, end stage disease of aggressive cancers.

Passive immunomodulation is also divided into nonspecific and specific therapies. Passive, nonspecific therapy includes the administration of cytokines such as systemic interferon or interleukin or cellular adoptive transfer mechanisms such as lymphocyte activated killer cells and interleukin-2 administered locally. Results of such therapy were inconsistent and yielded high clinical toxicities. When IL-2 is administered systemically, an unacceptable rate of systemic toxicity was observed including fever, malaise, hypotension, pulmonary edema and shock. Passive specific immunomodulation includes the administration of antibodies targeted to epidermal growth factor receptor, or through cellular adoptive transfer through T cells specific for the tumor.

7) Importance of Maintaining Exocytosis for Immune Recognition

As indicated above, in order to effectively kill cancer cells, it is crucial that cancer cells maintain their ability to undergo exocytosis. Exocytosis is the specific process by which a cellular vesicle fuses with the plasma membrane of the cell. It is the process by which proteins and lipids that are created inside a cell are transported to the cell's exterior. (Alberts B, et al. Molecular Biology of the Cell, Third Edition 1994, Garland Publishing pg. 626)

Proteins can be secreted from cells by exocytosis in either a constitutive or a regulated manner (Alberts, supra, page 633). In the regulated pathway, molecules are stored in secretory vesicles which do not fuse with the plasma membrane to release their contents until an extracellular signal is received. Whereas this pathway only operates in specialized selected cells, a constitutive secretory pathway operates in all cells, mediated by continual vesicular transport from the trans Golgi network to the plasma membrane. (Alberts, supra, pg 633). This method allows various membrane proteins, secreted proteins and lipids to be delivered to the appropriate plasma membrane domains (Alberts, supra, p 633).

An antigen is a macromolecule that includes virtually all proteins and many polysaccharides (Alberts, supra, p 1201). These so called antigenic determinants stimulate the production of antibodies or T cell responses (Alberts, supra, p. 1201). Because the immune system works by clonal expansion, even a single antigenic determinant will activate many clones. Conversely, the alteration or down regulation of antigenic determinants may predictably significantly alter the host's immune response to a tumor antigen.

Most TAA are self-antigens that are overexpressed or altered post-transcriptionally. In order to mount an adequate response, TAA-specific T cells and innate immunity mediated by non-specific activated T cells, activated NK cells and activated macrophages are necessary. With this in mind, there are two major reasons why tumors do not induce a vigorous immune response. First, the tumor can fail to provide a proper antigen for the immune response to detect and to which the immune system can react. Second the tumor can prevent an immune response by failing to provide accessory molecules essential for developing an immune response (Steele, supra.

Lack of appropriate antigen presentation can include expressing a mutant tumor protein that is not immunogenic, having a defective antigen processing pathway so that the antigen cannot be shuttled to the cell surface or by masking the tumor antigen so it cannot be seen by immune cells (Steele, supra). Without the tumor expression of essential surface molecules, no antitumor response can be generated (Steele, supra. These findings emphasize the need to have an intact method of exocytosis within cancer cells to allow TAAs to be expressed on cancer cells and to elicit an immune response.

It has been demonstrated that when cancer have a higher expression of Beta-2 macroglobulin, a component of the MHC-1, the clinical outcome improves (Feinmesser M et al. Eur Arch Otorhinolaryngol (2004) 261:359-368). It is suggested that the increased antigen expression facilitates tumor-antigen presentation to CD8 lymphocytes.

In addition to the expression of TAA, exocytosis is important in metastases. Cancer metastases is a process involving a coordinated program of events that includes changes in cell adhesion, polarized proteolysis and migration, intravasation into the circulation, subsequent adhesion to endothelial cells followed by extravasation, invasion and induction of angiogenesis. Cell surface proteins and receptors are intimately involved in these processes. For example, loss of E-cadherin can reduce cell-cell adhesion and allow cancer cells to more readily escape tumors. Integrins regulate cell adhesion, motility, invasion, and angiogenesis, and metalloproteases on tumor cells can degrade the extracellular matrix. In other words, the process of exocytosis, which on one hand may release metalloprotease and contribute to primary invasion of the primary site, is integrally important in the production of adhesion molecules which help prevent metastases and the expression of antigens that may facilitate recognition and destruction by the immune system. Any attempt to globally shut down the process of exocytosis may therefore have significant drawbacks in the therapy of cancer medicine.

In fact, the treatment of cancer includes attempts to enhance the immunogenicity of tumor cells. For example, one requirement for T cells to attack cancer cells is to bind to a specific peptide fragment that is presented on a cancer cell surface. It is known that tumor cells rarely express this antigen and efforts have been made to transduce costimuatory molecules in tumors to promote a vigorous antitumor immune response (Steele, supra).

8) Cholinergic Modulation of Immune Function

Cells that are normally immunoprotective from cancer include but are not limited to natural killer (NK) cells, activated macrophages, and T cells (including Tumor infiltrating lymphocytes and Natural killer T Cells) Acetylcholine inhibits natural killer cell function, which was blocked by atropine (Qiu Y H, Peng Y P, et al. Effect of acetylcholine on in vitro IL-2 production and NK cell cytotoxicity of rats. Lymphology 37(1):31-8, 2004)), suggesting that botulinum may inhibit suppression of NK cell activity. NK cells are known to induce apoptosis of malignant cells (Smyth M J, et al. Activation of NK Cell Cytotoxicity. Molec Immunol 42:501-510, 2005) and inhibit metastases (Kim, S, et al. In vivo natural killer cell activities revealed by natural killer cell-deficient mice. Proc Natl Acad Sci 97, 2000, abstract), hence botulinum may enhance this activity. Pilocarpine, an acetylcholine analog, increases the CD8/CD4 ratio which was also blocked by atropine, suggesting that T cell suppressor activity is positively influenced by acetylcholine (Prync A E, Arzt E, et al. The inhibitory effect of the muscarinic agonist pilocarpine on lymphocyte activation involves the IL-2 pathway and the increase in suppressor cell function. Int J. Neurosci 62, 1992, abstract). This would suggest that a reversal of the CD8/CD4 ratio or an increase in T helper activity would positively influence cancer cytotoxicity (Gerloni M, et al. Springer Seminars in Immunopathology, Springer-Verlag 2005, 1-15) as well. Acetylcholine also reduces tumor necrosis factor production (Steinman L. Elaborate interactions between the immune and nervous systems. Nature Immunology 5, 2004, abstract). Finally, when human salivary glands were injected with botulinum toxin, it was observed that the quantitative amount of immunoglobulin (specifically IgA) secreted into the saliva increased. The above findings support the use of botulinum to locally enhance immune cytotoxicity and humoral immunity.

9) Botulinum Toxin can Modulate the Immune System

The eventual alteration of immune function that is caused by cholinergic inhibition includes enhanced cellular and humoral immunity. Enhanced NK cell function directly enhances killing of cancer cells. Enhanced NK cell activity causes secondary enhancement of cellular and humoral immunity by release of cytokines and interferon gamma. This results in increased T cell and NKT cell function, which further enhances cellular destruction of cancer.

Enhanced NK cell function has also been demonstrated to reduce metastases (Kim, supra).

Enhanced NK cell function also enhances the outcome of patients with viral infections, viral diseases, viral-induced growths, autoimmune disease (such as sjogren's disease, insulin dependent diabetes), multiple sclerosis, chronic wounds, chronic infections such as tonsillitis (Ferlazzo G, et al. Journal Immunol 2004, 172:1455-1462) or bone infections (Miyasaki K, Periodontal Immunology, UCLA School of Dentistry Homepage), rheumatoid arthritis, myasthenia gravis and human immunodeficiency virus (HIV), all of which are conditions characterized by reduced NK cell numbers, function or activity (Baxter, A G, et al. Autoimmunity 2002, 35:1-14, and Lee PT, et al., J. Clin Invest 2002, 110: 793-800). Low NK cell activity is also found in Chronic fatigue syndrome (Whiteside T L, et al., AM J Med 105, 1998, abstract), and hepatitis (Chen Y, et al., J Viral Hepatitis 12, 2005, abstract), both of which are amenable to botulinum therapy.

CONCLUSION: Injecting botulinum toxin around but away from cancerous cells will improve local control of cancer at the primary site, prevent the distant spread of cancer cells into the circulation and will treat cancer cells in the local environment and distant circulations. The risks (as described above) of injecting the toxin into or into the vicinity of a cancer will be eliminated. Likewise, injecting botulinum toxin in this manner will enhance the outcome of patients suffering from viral infections, viral diseases, viral-induced growths, autoimmune diseases, multiple sclerosis, chronic wounds, chronic infections, rheumatoid arthritis, myasthenia gravis and HIV, etc., as described above.

Classification of Cancers Amenable to Treatment:

| Cancer Type | Specific Examples |
|---|---|
| Digestive/Intestinal cancers: | Salivary gland, lips, oral cavity, oropharyngeal, hypopharyngeal, nasopharyngeal, esophageal, stomach, small intestine, large intestine, anal |
| Nervous system cancers: | Brain, nerve |
| Hepatobiliary cancers: | Liver, gall bladder, pancreas, biliary tract |
| Genitourinary cancers: | Kidney, ureter, bladder, urethera, prostate, penile, vaginal, vulvar, uterine, endometrial, ovarian, cervical, testicular |
| Breast cancer: | |
| Respiratory cancers: | nose, sinus, nasopharyngeal, laryngeal, tracheal, bronchial, lung, pleura (mesothelioma) |
| Integument cancers: | melanoma, squamous cell carcinoma, basal cell carcinoma, merkel cell |
| Musculoskeletal: | rhabdomyosarcoma, sarcomas |
| Hematopoietic cancers: | lymphoma, leukemia, myelodysplasia |
| Sensory organs: | eye, ear |
| Endocrine: | thyroid, parathyroid |
| Neuroendocrine: | neuroendocrine cancers except those of the adrenal medulla or glomus tumors |

Treatment of Cancer Requires the Control of Metastases

Inhibition of spread: Physically manipulating or squeezing a cancer at the gross or microscopic level through contractile cells may produce a physical pressure for the cancer cells to spread, or it may allow cancer cells that have already entered into an efferent channel to be squeezed into the broader circulation. For example, a well-known premise in oncologic surgery is to minimize manipulation of the cancer during resection to minimize the physical forces that may lead to entrance and spread of cancer cells into tubules such as lymphatics or blood vessels. In fact, when surgically feasible, it is desirable to initially ligate the vessels of a cancer to the cancer and minimize spread.

Botulinum Toxin Will Locally Denervate Muscular Tissue

Botulinum toxin will inhibit contraction of gross or microscopic muscular fibers around a cancer thereby inhibiting the chance of squeezing the cancer cells into the local environment or into efferent tubules that carry cancer distantly. Botulinum toxin will paralyze the lymphatic muscle that contracts to squeeze lymph and possibly cancer cells into the distant circulation.

Treatment of Cancer Requires the Ability to Positively Immunomodulate

Botulinum may enhance local immunoglobulin production when applied to a mucosal surface. This may enhance 'tumor-killing' cells or properties of the local tissue and enhance the anti-cancer effect.

Botulinum has been shown to enhance and/or cause proliferation of a 'myoepithelial cell' which is a very specific cell type. The myoepithelial cell is considered an essential defensive cell in breast cancer for unknown mechanisms. By enhancing proliferation of these myoepithelial cells, botulinum may enhance the host defense mechanism in tumors that have myoepithelial cells (breast, prostate, lung, airway, etc. . . . ).

Other unknown mechanisms may also be at play. For example, cell-cell signaling and subsequent growth/metastasis is a feature of cancer cells. It has been suggested that by altering these signals, one may alter the growth of cancer. Regarding botulinum, the signals can be chemical (i.e. substances released by exocytosis and blocked by botulinum) or physical (i.e. physical signals to surrounding cells) but either can be blocked by botulinum.

Techniques that target multiple sequences of events in cancer progression are more likely to benefit than a technique that targets only one sequence.

EXAMPLES

The following example demonstrates the ability of botulinum toxin to enhance a cellular immune response:

Example #1

A patient with verruca vulgaris (common wart) is injected at the base of the wart and its periphery with a total of 25 units of botulinum toxin type A. Over 3-5 weeks, it is noticed that the size of the lesion is significantly reduced in all dimensions (by nearly 90%), is soft and is barely perceptible. After 3 months, the size of the lesion returns to its original size.

The following prophetic examples demonstrate how the invention will work.

Example #2

A 50 year old diagnosed with invasive lung cancer undergoes local administration of 30 units of botulinum toxin type A around the cancer by bronchoscopic injection, aerosolization or transthoracic injection. The cancer is visualized either clinically or radiographically and the area around the cancer is directly injected, and the patient undergoes radiation, chemotherapy or surgery as initially planned. The local application of botulinum also enhances the patient's local immunity which serves to minimize infection during therapy, leading to fewer episodes of pneumonia and fewer interruptions in treatment because of infection. After 2 months of standard cancer therapy, it is noted that the local invasion and regional and distant spread is reduced. The patient experiences an improved clinical outcome.

In the above example, the patient's regional or distant lymph node or nodes, thymus, spleen or bone marrow can each also be injected with 1-100 units of botulinum toxin type A. The tissues are injected by radiographic guidance or direct visualization during mediastinoscopy or surgery. Following injection, it is noticed that there is an improved immunologic response to the cancer. Local control and local, regional and distant metastases are reduced. The injection may be repeated in 3-6 month intervals.

Example #3

A 50 year old man with invasive prostate cancer is injected with 40 units of botulinum toxin type A around the cancer which results in fewer regional or distant metastases. The injection is guided to the region around the cancer by radiographic guidance (cat scan, ultrasound, MRI guidance or others). The effect of botulinum is also on local myoepithelium and the incidence of in-transit, regional and distant metastasis is reduced. The patient continues to undergo standard therapy for the prostate cancer. During the course of treatment there is less invasion of surrounding tissue and less spread of cancer cells into the regional or systemic circulation. The patient is reevaluated periodically and it is noted that the cancer and cancer-region requires reinjection in 3 months, as the patient has persistent disease that did not respond to standard therapy. 40 more units are injected and the patient continues with planned therapy. Three months later the tumor is eliminated and further injections are not required. The patient experiences an improved cure and survival.

The patient's regional or distant lymph nodes, thymus, spleen or bone marrow can each also be injected with 1-100 units of botulinum toxin type A. These tissues are injected by radiographic guidance, direct palpation or during surgery. Local control and local, regional and distant metastases are reduced. The injection may be repeated in 3-6 month intervals.

Example #4

A 60 year old female diagnosed with breast cancer is treated with 30 units of botulinum toxin type A injected around the cancer before any therapy begins. Local contraction of breast tissue is reduced and the patient experiences a reduced incidence of local, regional and distant spread. Clinical outcome is improved.

The patient's regional or distant lymph nodes, thymus, spleen or bone marrow can each also be injected with 1-100 units of botulinum toxin type A. The lymph nodes are injected by palpation, radiographic guidance or direct visualization during surgery. Following injection, it is noticed that there is an improved immunologic response to the cancer. Local control and local, regional and distant metastases are reduced. The injection may be repeated in 3-6 month intervals.

Alternatively, the patients sentinel lymph node can be identified using lymphoscintigraphy. Since these nodes are highly likely to contain metastatic cancer, they are avoided during radiographic injections, and only the surrounding nodal basin is injected.

Example #5

A 45 year old male is diagnosed with locally invasive colon cancer. At the time of diagnosis, 50 units of botulinum toxin type A are injected into and/or around the cancer to weaken the contractile effects of the gross and microscopic colonic musculature. The cancer is 'frozen' and there is less invasion of cancer cells into the surrounding tissue or lymphatic or blood vessels. The patient can undergo additional therapy (chemotherapy, radiation therapy and/or surgery) and local, regional and distal spread is reduced or eliminated.

The patient's regional or distant lymph nodes, thymus, spleen or bone marrow can each also be injected with 1-100 units of botulinum toxin type A. These tissues are injected by radiographic guidance, endoscopic injection, direct palpation or during surgery. Local control and local, regional and distant metastases are reduced. The injection may be repeated in 3-6 month intervals.

Example #6

A patient with metastatic tongue cancer is noted to have symptoms of compression and bleeding referable to local invasion of a regional metastasis. The metastasis is deemed nonoperable and he cannot receive any further radiotherapy. Alternatively, he may be treated with surgery, radiotherapy or chemotherapy. The area around the metastatic lesion is injected with 30 units of botulinum toxin type A. There is less local invasion and metastases from the lesion. The metastasis undergoes regression and compressive symptoms are reduced.

The patient's regional or distant lymph nodes, thymus, spleen or bone marrow can each also be injected with 1-100 units of botulinum toxin type A. These tissues are injected by radiographic guidance, direct palpation or during surgery. Local control and local, regional and distant metastases are reduced. The injection may be repeated in 3-6 month intervals.

Example # 7

A 35 year old male has locally invasive pharyngeal cancer. Thirty five units of botulinum toxin Type A is injected around the lesion. It is noticed that the cancer undergoes regression and is eliminated with local injections of botulinum without further therapy.

The patient's regional or distant lymph nodes, thymus, spleen or bone marrow can each also be injected with 1-100 units of botulinum toxin type A. These tissues are injected by radiographic guidance, direct palpation or during surgery. Local control and local, regional and distant metastases are reduced. The injection may be repeated in 3-6 month intervals.

Alternatively, the patient's sentinel lymph node can be identified using lymphoscintigraphy. Since these nodes are highly likely to contain metastatic cancer, they are avoided during radiographic injections, and only the surrounding nodal basin is injected.

Example #8

A patient with cancer has invasive fungal sinusitis. His white blood count is less than 1,000 and there is a poor immunologic response in the sinus cavity. He is taken to surgery for remove of the tissue invaded by the fungus. Before surgery or preferably, after removal of the tissue and during surgery, 10 units of botulinum toxin type A are injected in multiple sites into the surrounding nasal cavity. It is noted that the local immunologic and systemic immunologic responses are improved and the patient experiences a cure from the disease.

The patient's regional or distant lymph nodes, thymus, spleen or bone marrow are each injected with 1-100 units of botulinum toxin type A. These tissues are injected by radiographic guidance, direct palpation or during surgery. Local control and distant spread of the fungus are reduced. The injection may be repeated in 3-6 month intervals.

Example #9

A patient with cancer, autoimmune disease, diabetes, HIV or AIDS or lupus has toenail fungus (onychomycosis). The affected nail is injected with 5 units of botulinum toxin type A in multiple spots and there is regression of the symptoms of onychomycosis. Alternatively, the surrounding normal tissues or regional lymph nodes can be injected.

Example #10

A 10 year old patient with insulin dependent diabetes mellitus (IDDM) is dependent upon insulin injections. Botulinum toxin type A (50 units) is injected using radiographic guidance into her pancreas. It is noticed that her natural insulin levels rise and she has fewer symptoms of diabetes.

Example #11

A 40 year old woman with autoimmune disease is injected with type A botulinum toxin. 100 units of the toxin are injected into her spleen, bone marrow or regional nodal basin where the symptoms are located. Following injection, her symptoms are improved.

Example #12

A 35 year old male with AIDS has a suppressed T helper population and is susceptible to infections. 50 units of botulinum toxin type A is injected into his thymus and spleen. Alternatively, his bone marrow can be injected. The patient's T cell population increases and his condition is significantly improved.

As noted above, Botulinum toxin is available from multiple sources. In addition, it is available from Allergan as Botox®, a BTX-A formulation; DySport®, another BTX-A preparation available in Europe from Ipsen, Ltd; and Myobloc™ (or NeuroBloc® in Europe), a BTX-B preparation available from Elan Pharmaceuticals.

Botulinum for use in the present invention can also be made by known pharmaceutical techniques by, for example, dissolving pharmaceutically acceptable Botulinum toxin in a pharmaceutically acceptable carrier useful for injection, such that the Botulinum is dissolved to the desired strength or concentration. These preparations can be made fresh or premade. Other pharmaceutically acceptable ingredients, such as preservatives, can be added. These preparations are made by techniques known in the art.

The amount of Botulinum toxin to use varies, of course, according to the size of the tumor to be treated. The maximum dosage of Botulinum A to administer should not exceed 500 units per injection session. Preferably, 0.01-100 units of Botulinum A should be used. More preferably, the dosage of Botulinum A should be in the range of from about 1 unit to about 50 units. Even more preferably, the dosage of Botulinum A should be in the range of from about 5 units to about 40 units.

It is known that an electric current can enhance the absorption of botulinum toxin into tissues. Black, et al., 1: Cell Biol—1986 August; 103(2): 535-44; Hesse, et al., 1: Neurosci Lett. 1995 Dec. 1; 201(1) 37-40; Hesse, et al., 1: Clin. Rehabil. 1998 October; 12(5): 381-8. Accordingly, one embodiment of the present invention would be to apply an electric current to or around the area to be treated. This should decrease the amount of botulinum toxin needed for effective results.

If a different neurotoxin is used, such as Botulinum B, C, D, E F or G, the dosage should conform to the above dosage for Botulinum A. Conversions, known in the art, can be used to calculate these dosages.

The above description sets forth various embodiments of the invention. This description, however, is not intended to be limiting on the scope of the invention.

What is claimed is:

1. A method of weakening or paralyzing the muscle fibers surrounding a neoplasm in a patient, comprising applying to the non-cancerous area around said neoplasm a therapeutically effective amount of botulinum toxin such that the therapeutically effective amount of the botulinum toxin reduces the spread of cells from the neoplasm, thereby inhibiting the growth or metastases of the neoplasm.

2. The method of claim 1, wherein the neoplasm is selected from the group consisting of digestive/intestinal, nervous system, heptobiliary, genitourinary, breast, respiratory, integament, musculoskeletal, hematopoietic, sensory organ, endocrine or neoendocrine neoplasms.

3. The method of claim 1, wherein the botulinum toxin is botulinum toxin type A.

4. The method of claim 1, wherein the dose of botulinum toxin does not exceed 500 units per application.

5. The method of claim 4, wherein the dose of botulinum toxin is between 0.01 and 100 units per application.

6. The method of claim 5, wherein the dose of botulinum toxin is between about 1 unit to about 50 units per application.

7. The method of claim 1, wherein the botulinum toxin is applied topically or by injection.

8. The method of claim 7, wherein the botulinum toxin is applied by injection.

9. A method of weakening or paralyzing the muscle fibers surrounding a neoplasm in a patient, comprising injecting into the non-cancerous area around said neoplasm a therapeutically effective amount of botulinum toxin type A such that the therapeutically effective amount of the botulinum type A reduces the spread of cells from the neoplasm, thereby inhibiting the growth or metastases of the neoplasm.

* * * * *